(12) United States Patent
Xu et al.

(10) Patent No.: US 9,168,230 B2
(45) Date of Patent: Oct. 27, 2015

(54) TETRARY GENE DELIVERY SYSTEM FOR GENE THERAPY AND METHODS OF ITS USE

(75) Inventors: Peisheng Xu, Chapin, SC (US); Remant Bahadur K.C., Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 13/477,701

(22) Filed: May 22, 2012

(65) Prior Publication Data
US 2012/0301512 A1    Nov. 29, 2012

Related U.S. Application Data

(60) Provisional application No. 61/519,666, filed on May 26, 2011.

(51) Int. Cl.
| | | |
|---|---|---|
| A61K 48/00 | (2006.01) | |
| A61K 9/51 | (2006.01) | |
| A61K 9/50 | (2006.01) | |
| C12N 15/87 | (2006.01) | |

(52) U.S. Cl.
CPC ............. *A61K 9/5184* (2013.01); *A61K 9/5036* (2013.01); *A61K 9/5161* (2013.01); *C12N 15/87* (2013.01)

(58) Field of Classification Search
None
See application file for complete search history.

(56) References Cited

U.S. PATENT DOCUMENTS

2005/0112172 A1*   5/2005   Pacetti .......................... 424/423

OTHER PUBLICATIONS

Xu et al., Gene delivery through the use of a hyaluronate-associated intracellularly degradable crosslinked polyethyleneimine, Biomaterials, 2009, vol. 30, pp. 5834-5843.*
Vinogradov, et al. Short biodegradble polyamines for gene delivery and transfection of brain capillary endothelial cells, J. Controlled release, 2010, vol. 143, pp. 359-366.*
Pack et al., Design and development of polymers for gene delivery, Nature Review, Drug Discovery, 2005, vol. 4, pp. 581-593.*
Mao et al, Charge Density and Molecular weight of polyphosphoramidate gene carrier are key parameters influencing its DNA compaction ability and transfection efficiency, Biomacromolecules, 2010, vol. 11, pp. 3432-3439.*
Bagai et al. Potential of mean force of polyehtylenimine-mediated DNA attraction, the Journal of Physical Chemistry B, 2013, vol. 117, pp. 49-56.*
Chen et al. Design of Serum Compatible Tetrary Complexes for Gene Delivery, Macromol. Biosci. 2012, vol. 12, pp. 637-646., publication of the instant application.*
Jeong et al. "Molecular design of functional polymers for gene therapy" Progress in Polymer Science 2007, 32, 1239-1274.
Mohajer et al. "Enhanced Intercellular Retention Activity of Novel pH-sensitive Polymeric Micelles in Wild and Multidrup Resistant MCF-7 Cells" Pharmaceutical Research 2007, 24 (9), 1618-1627.
Lee et al. "Tumor pH-responsive flower-like micelles of poly(L-lactic acid)-b-poly(ethylene glycol)-b-poly(L-histidine)" Journal of Controlled Release 2007, 123, 19-26.
Boussif et al. "A versatile vector for gene and oligonucleotide transfer into cells in culture and in vivo: Polyethylenimine" Proceedings of the National Academy of Sciences 1995, 92, 7297-7301.
Fischer et al. "In vitro cytotoxicity testing of polycations; influence of polymer structure on cell viability and hemolysis" Biomaterials 2003, 24, 1121-1131.
Ito et al. "Hyaluronic acid and its derivative as a multi-functional gene expression enhancer: Protection from non-specific interactions, adhesion to targeted cells, and transcriptional activation" Journal of Controlled Release 2006, 112, 382-388.
Xu et al. "Gene delivery through the use of a hyaluronate-associated intracellularly degradable crosslinked polyethyleneimine" Biomaterials 2009, 30, 5834-5843.
Bahadur K.C et al. "Design of Serum Compatible Tetrary Complexes for Gene Delivery" Macromolecular Bioscience 2012, 10.1002, 1-10.
Ou et al. "A family of bioreducible poly(disulfide amine)s for gene delivery" Biomaterials 2009, 30, 5804-5814.

* cited by examiner

*Primary Examiner* — Bethany Barham
*Assistant Examiner* — Ping Cao
(74) *Attorney, Agent, or Firm* — Dority & Manning, P.A.

(57) ABSTRACT

Delivery systems and their methods of formation are generally provided. The delivery system can protect a delivery molecule (e.g., DNA/RNA) and deliver it into a cell via serum. In one embodiment, the method can include binding a delivery molecule with polyethylenimine such that an end of the delivery molecule is exposed; capping the end of the delivery molecule with a first biocompatible polymer to form a core; and encapsulating the core with a second biocompatible polymer. The resulting delivery system can include a delivery molecule bonded with polyethylenimine such that an end of the delivery molecule is exposed; a first biocompatible polymer electrostatically bonded to the end of the delivery molecule to form a core; and a second biocompatible polymer encapsulating the core.

5 Claims, 7 Drawing Sheets

TETRARY GENE DELIVERY SYSTEM FOR GENE THERAPY AND METHODS OF ITS USE

PRIORITY INFORMATION

The present application claims priority to U.S. Provisional Patent Application Ser. No. 61/519,666 titled "Tetrary Gene Delivery System for Safe and Efficient Gene Therapy" of Xu, et al. filed on May 26, 2011, the disclosure of which is incorporated by reference herein.

BACKGROUND

Gene delivery has been extensively explored as a promising therapeutic tool for treating genetic diseases or producing animal disease models. Due to the growing concern about the safety of viral vectors, non-viral gene delivery system was proposed as an alternative. Among those non-viral vectors that have been investigated, polyethylenimine (PEI) is one of the most widely used polymers. PEI forms polyplexes with DNA molecules due to the electrostatic interaction. After uptake by cells, PEI induces "proton sponge effect" and promotes the endosomal escaping of polyplexes.

Thus, PEI has been considered as a benchmark for non-viral vectors; however, the in vivo therapeutic application of PEI has been hampered due to several issues. First, the PEI/DNA polyplexes system is not compatible with serum, which is the main cause for low transfection efficiency. Second, PEI is cytotoxic and can cause cell death and possible organ damage if applied in vivo. Third, PEI as well as other non-viral vectors is much less efficient than viral vectors.

To decrease the cytotoxicity and further increase its transfection efficiency, PEI has been formulated with polysaccharide-based polyanions, such as hyaluronic acid. From our previous study, we found that the PEI/HA system did increase the transfection efficiency and decreased cytotoxicity; however, it was not resistant to the high concentration of serum which exists in in vivo conditions.

Thus, conventional non-viral gene delivery vectors are not compatible with serum, which hampers their in vivo applications. As such, a need exists for a non-viral gene delivery system (PoSH) which is compatible with serum.

SUMMARY

Objects and advantages of the invention will be set forth in part in the following description, or may be obvious from the description, or may be learned through practice of the invention.

Methods are generally provided for forming a delivery system, which can, in certain embodiments, protect a delivery molecule (e.g., DNA/RNA) and deliver it into a cell via serum. In one embodiment, the method can include binding a delivery molecule with polyethylenimine such that an end of the delivery molecule is exposed; capping the end of the delivery molecule with a first biocompatible polymer to form a core; and encapsulating the core with a second biocompatible polymer.

The polyethylenimine can, in most embodiments, have a positive electrostatic charge, and the end of the delivery molecule can have a negative electrostatic charge. As such, the polyethylenimine can be electrostatically bonded to the end of the delivery molecule.

Additionally, the end of the delivery molecule can, in certain embodiments, have a negative electrostatic charge, while the first biocompatible polymer has a positive electrostatic charge. As such, the first biocompatible polymer can be electrostatically bonded to the end of the delivery molecule The core can also have a positive electrostatic charge, and the second biocompatible polymer can have a negative electrostatic charge, such that the second biocompatible polymer is electrostatically bonded to the core.

The first biocompatible polymer can be, in certain embodiments, a polyamine (e.g., a polyspermine polymer or derivative), N,N'-bis(3-aminopropyl)-1,3-propanediamine, N,N'-bis(3-aminopropyl)-ethylenediamine, N,N'-bis(2-aminoethyl)-1,3-propanediamine, triethylenetetramine, or copolymers thereof or mixtures thereof.

Delivery systems are also generally provided, such as those formed via the disclosed methods. In one embodiment, the delivery system can include a delivery molecule (e.g., DNA/RNA) bonded with polyethylenimine such that an end of the delivery molecule is exposed; a first biocompatible polymer (e.g., a polyamine, such as polyspermine) electrostatically bonded to the end of the delivery molecule to form a core; and a second biocompatible polymer (e.g., hyaluronate) encapsulating the core.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

FIG. 3 shows an agarose gel retardation assay of di-thiol cleaved polyplexes by DTT. Complexes formed at N/P ratio of 10 with PEI25 were coated with PSP (N/P ratio 50) and HA (w/w ratio 2). Then, the complexes were incubated with DTT (10 mM) for 3 h and heparin (5%) for 2 h at room temperature. DTT showed a significant effect in the complexes with PSP polymers.

FIG. 4 shows dye exclusion assay of complexes. Complexes formed with PEI25 (N/P ratio 10) were coated with PSP (N/P ratio 10, 20 and 50) and HA (w/w ratio 2). Then, it was incubated with DTT (10 mM) for 3 h and heparin (5%) for 2 h. 100 μL of dye (1×SYBR Green I) was added to each sample. Data represent mean±STD (n=3).

FIG. 5 shows the in vitro EGFP gene expression in NIH/3T3 cells as the function of PSP and HA. Note that the gene transfection experiment was performed in the presence of 10% (A, B), 25% (B,C) and 50% (E, F) serum using PEI25 and Lipo2000 as positive control and cells without any treatment as negative control. Transfection efficiency of the polymers without HA is negligible in all study where as with HA it was dependent in the content of PSP. Data represent percentage of EGFP positive cells (mean±SD, n=3).

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

As used herein, a molecule having a negative electrostatic charge can also be referred to as an anion or anionic, and a molecule having a positive electrostatic charge can also be referred to as a cation or cationic. Also, electrostatic bonding or electrostatic interaction refers to the tendency of oppositely charged molecules to attract to each other, such as through van der Waals forces, ionic bonding, hydrogen bonding, etc.

A non-viral gene delivery system (PoSH) that is compatible with serum is generally provided, along with methods of making and using the same. The PoSH system shows non-toxic effect to cells and higher transfection efficiency than the commercialized transfection regent. Furthermore, this system can display high transfection efficiency at 50% serum condition. Thus, this non-viral gene delivery system is applicable to: gene therapy, gene delivery, DNA delivery, siRNA delivery, RNAi, research tool, gene vaccine, cancer gene therapy, Alzheimer's disease gene therapy, and/or animal model construction.

Generally speaking, the delivery system includes a delivery molecule (e.g., DNA, RNA, etc.) bonded with a polyethylenimine such that an end of the delivery molecule is exposed. In one embodiment, one or both ends of the delivery molecule can have a negative electrostatic charge, while the polyethylenimine forms a polymeric matrix having a positive electrostatic charge. Thus, the polyethylenimine can be, in certain embodiments, electrostatically bonded to one end of the delivery molecule, while leaving the opposite end or a part of the delivery molecule exposed.

Polyethylenimine is particularly suitable for this delivery system due to its excellent DNA condensation capacity. PEI can be branched PEI or linear PEI, and can be synthesized by polymerization of aziridine. In one particular embodiment, branched PEI (e.g., molecular weight of about 25 kDa) can form polymer/DNA polyplexes at N/P ratio of about 2 or more. As used herein and commonly known in the art, the term "N/P ratio" refers to the molar ratio of the number of nitrogens "N" in the polymer to the number of phosphates "P" in the DNA/RNA molecule. In one embodiment, the N/P ratio for the PEI and delivery molecule can be greater than about 2, such as about 2 to about 50. In one particular embodiment, the N/P ratio for the PEI and delivery molecule can be about 5 to about 15, such as about 10.

In one embodiment, the molecular weight of the PEI can be relatively high, such as greater than about 5 kDa (e.g., about 20 kDa to about 30 kDa). However, any suitable PEI polymer can be utilized in the present delivery system.

In the system, a first biocompatible polymer is utilized to cap the exposed end of the delivery molecule to form a core. In one particular embodiment, when the end of the delivery molecule has a negative electrostatic charge, the first biocompatible polymer can have a positive electrostatic charge. As such, the first biocompatible polymer can be, in certain embodiments, electrostatically bonded to the end of the delivery molecule. Thus, the resulting core can have a positive electrostatic charge, particularly about its outer surface.

Particularly suitable biocompatible polymers that can be used as the first biocompatible polymer in the present system can include, but are not limited to, a polyamine polymer, N,N'-bis(3-aminopropyl)-1,3-propanediamine, N,N'-bis(3-aminopropyl)-ethylenediamine, N,N'-bis(2-aminoethyl)-1,3-propanediamine, triethylenetetramine, or copolymers thereof or mixtures thereof.

For example, one particularly suitable first biocompatible polymer is a polyspermine polymer, which is a particular type of polyamine polymer. Polyspermine can be formed via reaction of spermine and a crosslinker in a molar ratio of about 5:1 to about 1:5. The resulting polyspermine polymer can, in certain embodiments, have a molecular weight of about 1 kDa to about 1,000 kDa. A 1:1 molar ratio of spermine and a crosslinker can form the highest molecular weight polymer of polyspermine.

The crosslinker utilized to form the polyspermine polymer can be any suitable crosslinker, such as Lomant's reagent (i.e., dithiobis(succinimidyl propionate) or "DSP"), cystamine bisacrylamide, bisacryloyloxyethyl) disulfide, or derivatives thereof or mixtures thereof. Without wishing to be bound by any particular theory, it is believed that the protonated nitrogen of the resulting PSP polymer electrostatically bonds with the negative (i.e., anionic) charge on the exposed end of the delivery molecule (e.g., DNA/RNA) to form a cap thereon.

In one embodiment, the N/P ratio for the first biocompatible polymer (e.g., polyspermine) and the delivery molecule (e.g., DNA/RNA) can be greater than about 5, such as about 5 to about 50.

A second biocompatible polymer is now utilized to encapsulate the core (e.g., by forming a shell about the core). In one embodiment, the second biocompatible polymer can have a negative electrostatic charge that electrostatically bonds to the core, particularly when the core has a positive electrostatic charge. One particularly suitable polymer that can be used as the second biocompatible polymer comprises hyaluronate, although any suitable polymers can be utilized (e.g., alginate). Hyaluronate (also called hyaluronic acid or hyaluronan or HA) is an anionic, nonsulfated glycosaminoglycan.

In one particular embodiment, the second biocompatible polymer can be present in a weight ratio of up to about 50, such as about 0.2 to about 50, comparing the weight of the delivery molecule.

Figure 1:
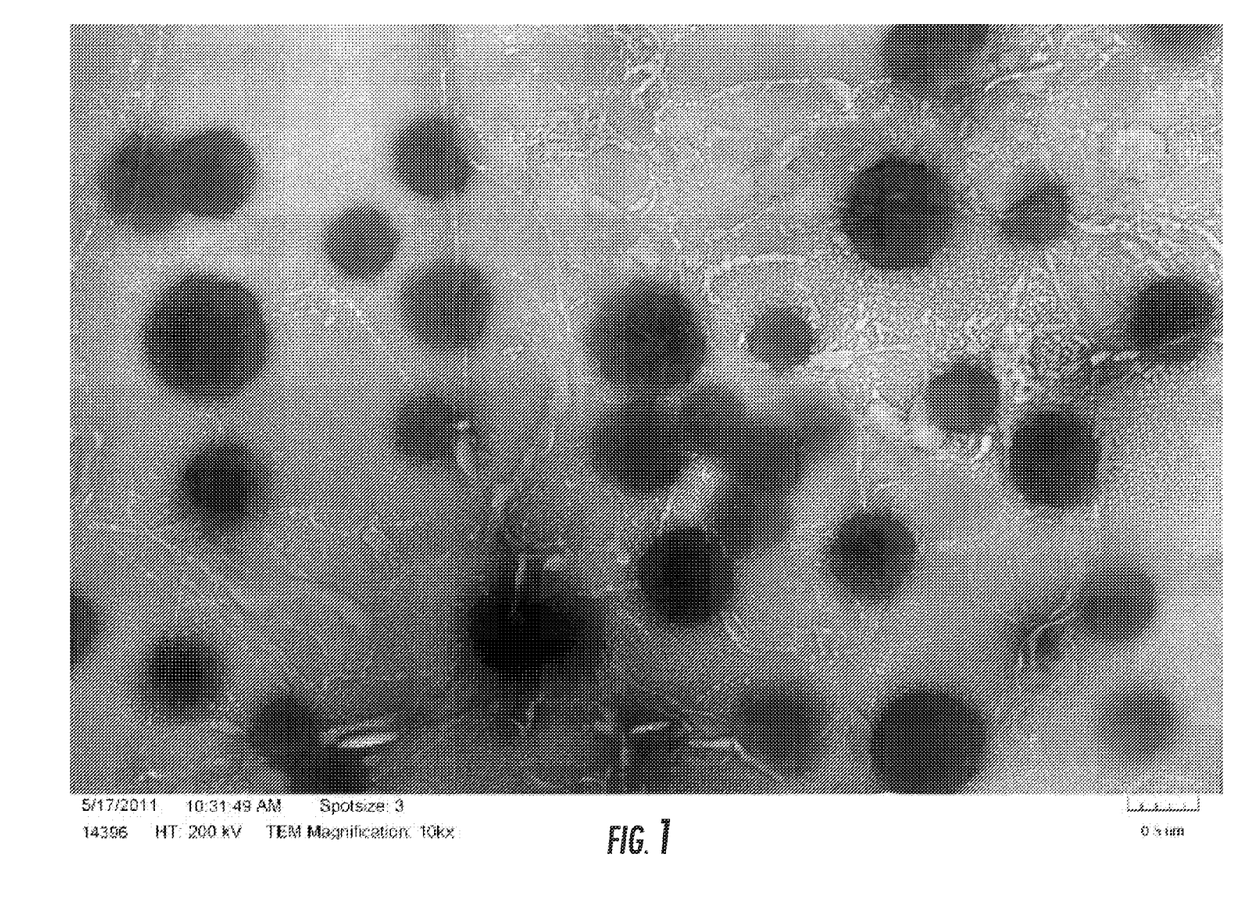
FIG. 1 shows TEM image of PoSH polyplexes with the composition of 10PEI50PSP2HA (scale bar is 500 nm) according to the Examples.
Figure 2:
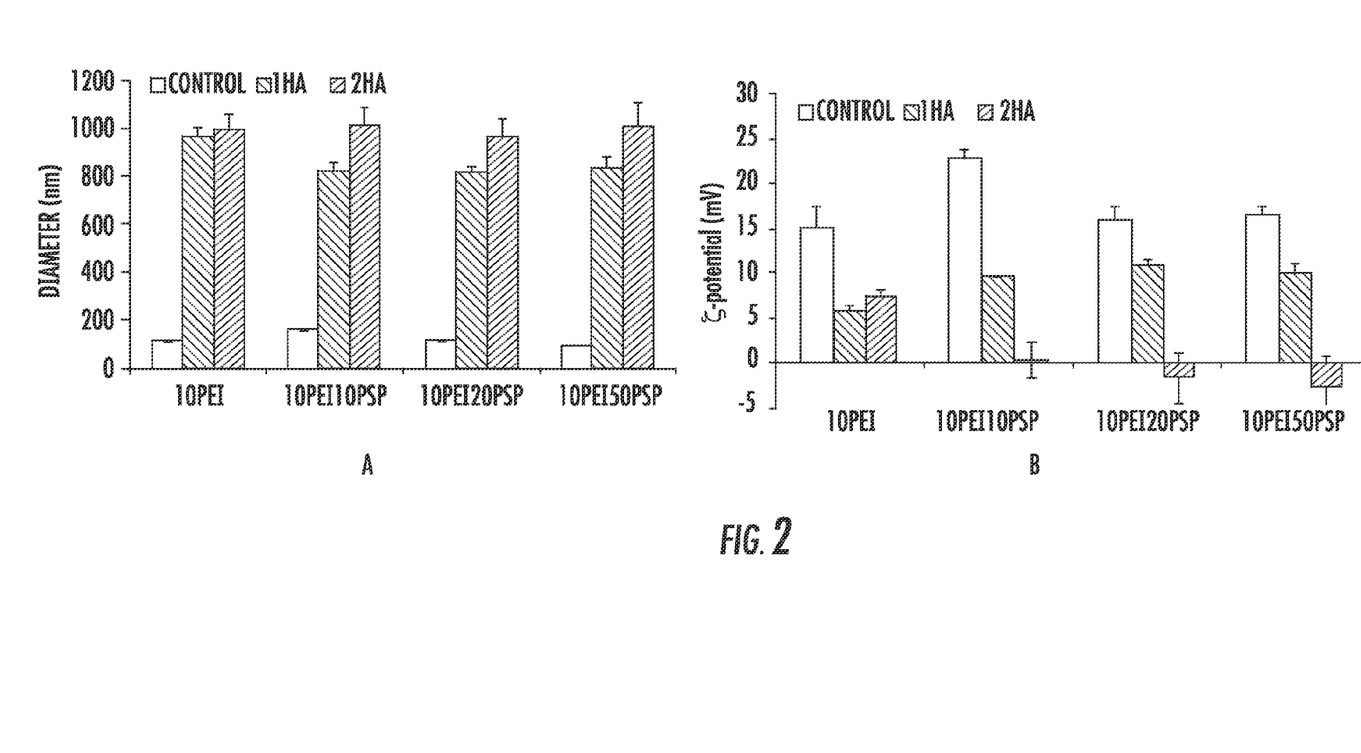
FIG. 2 shows the hydrodynamic size (2A) and ξ-potential (2B) of complexes in 150 mM NaCl at room temperature according to the Examples (data represent mean±STD, n=3). The size of the complexes was significantly increased with the addition of HA where ξ-potential was decreased. The effect was substantial in ξ-potential as compared to the size.
Figure 3:
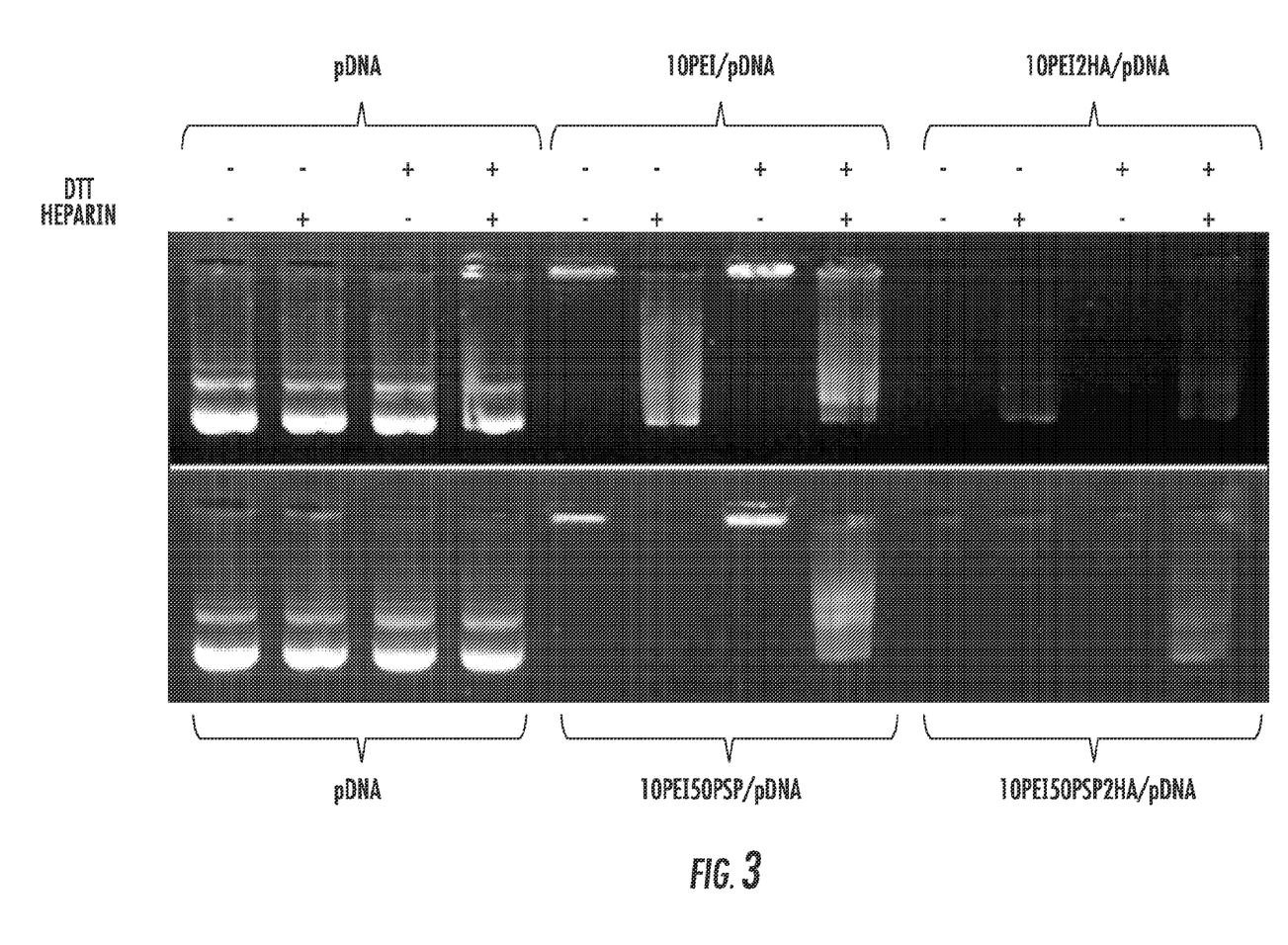
Figure 4:
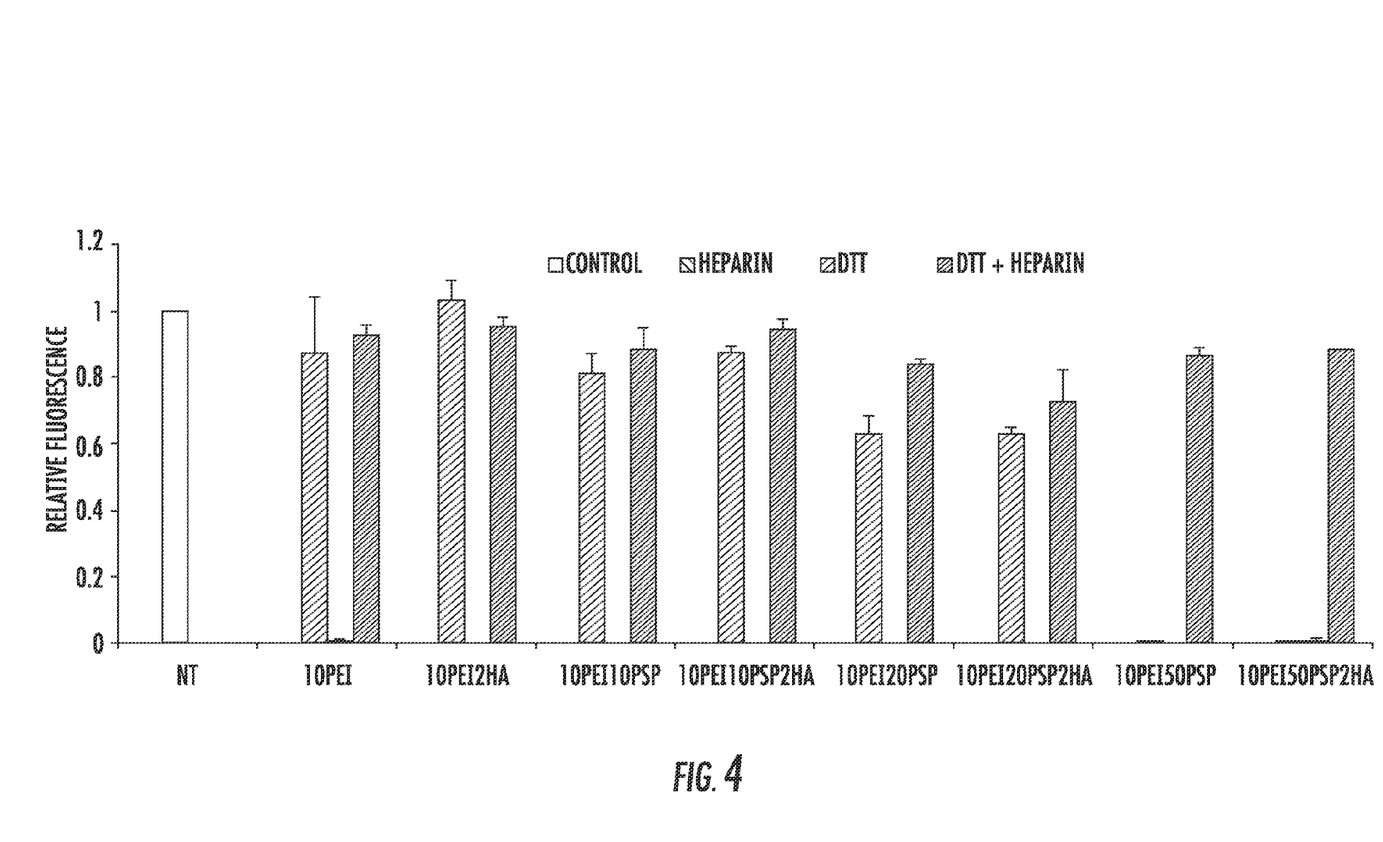
Figure 5:
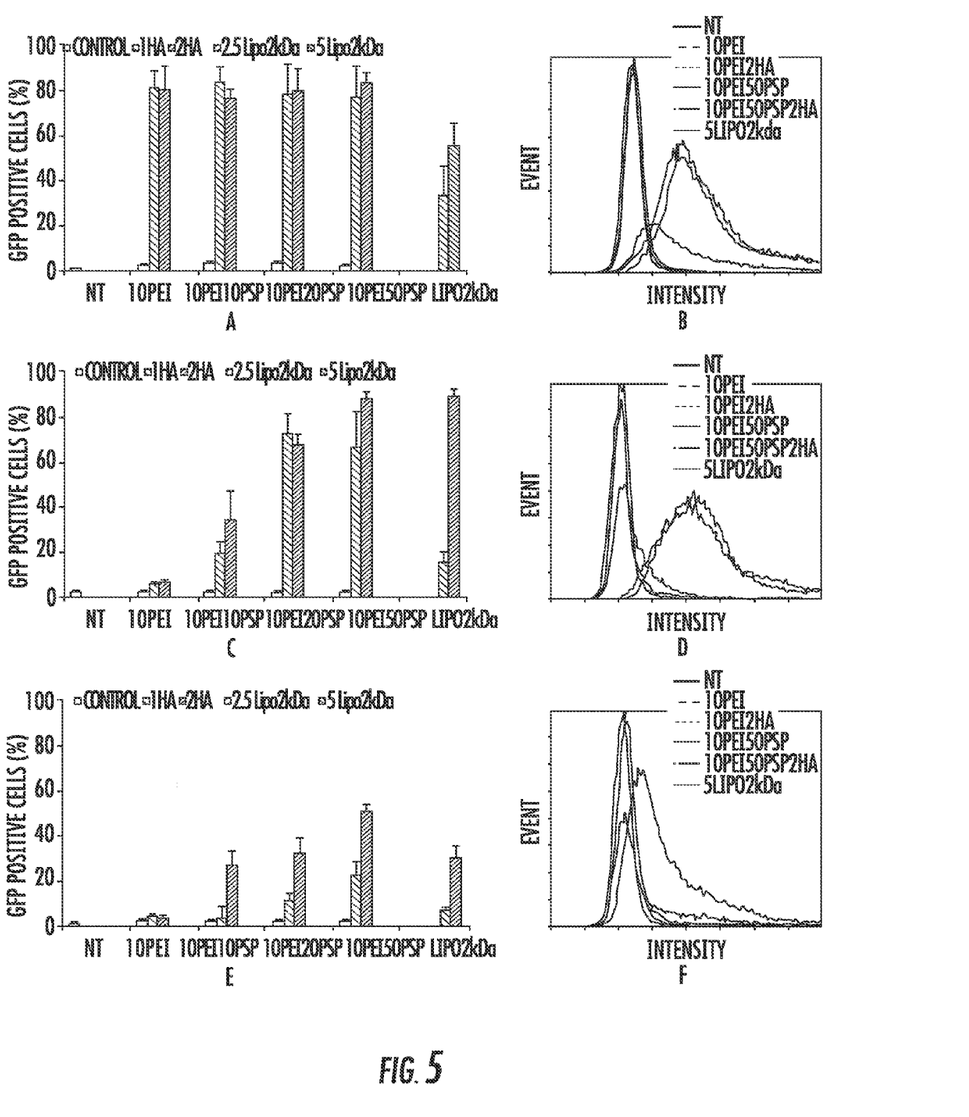
Figure 6:
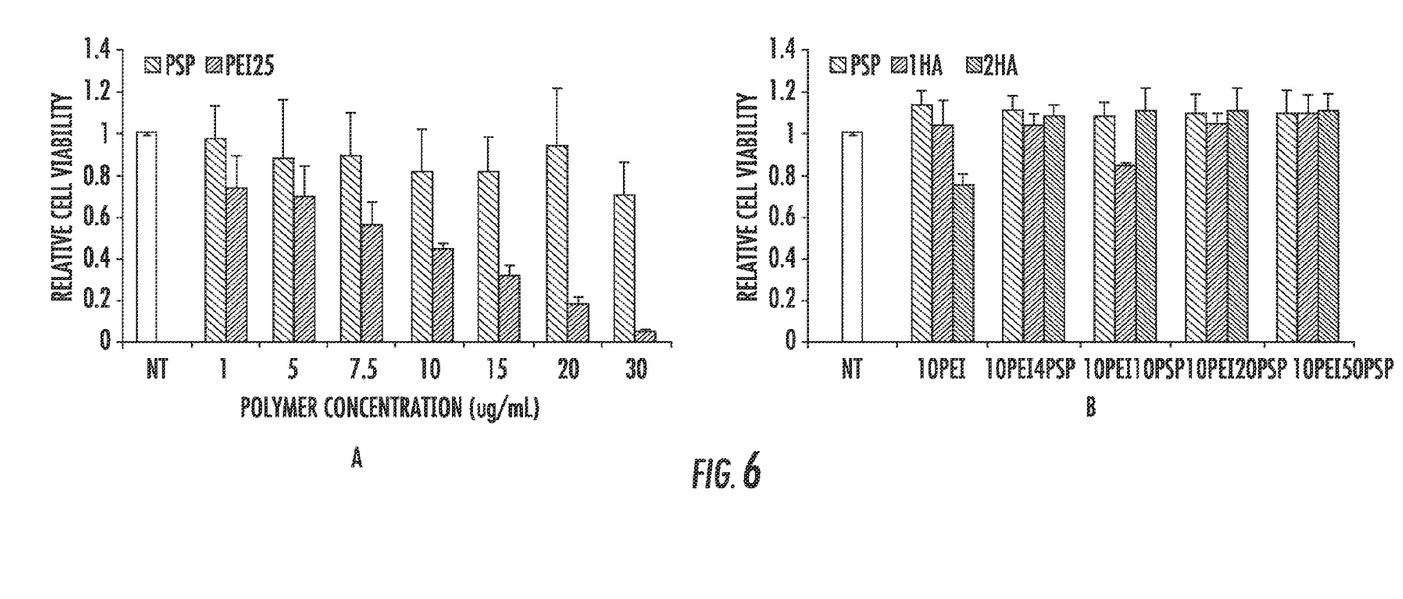
FIG. 6 shows the viability of NIH/3T3 cells treated with of polymers (A) and complexes (B), evaluated by MTT assay. Data represent mean±SD, n=3. PSP polymer is almost non-toxic even at 30 μg/mL, which was used for transfection study and the complexes were also not-toxic at all.
Figure 7:
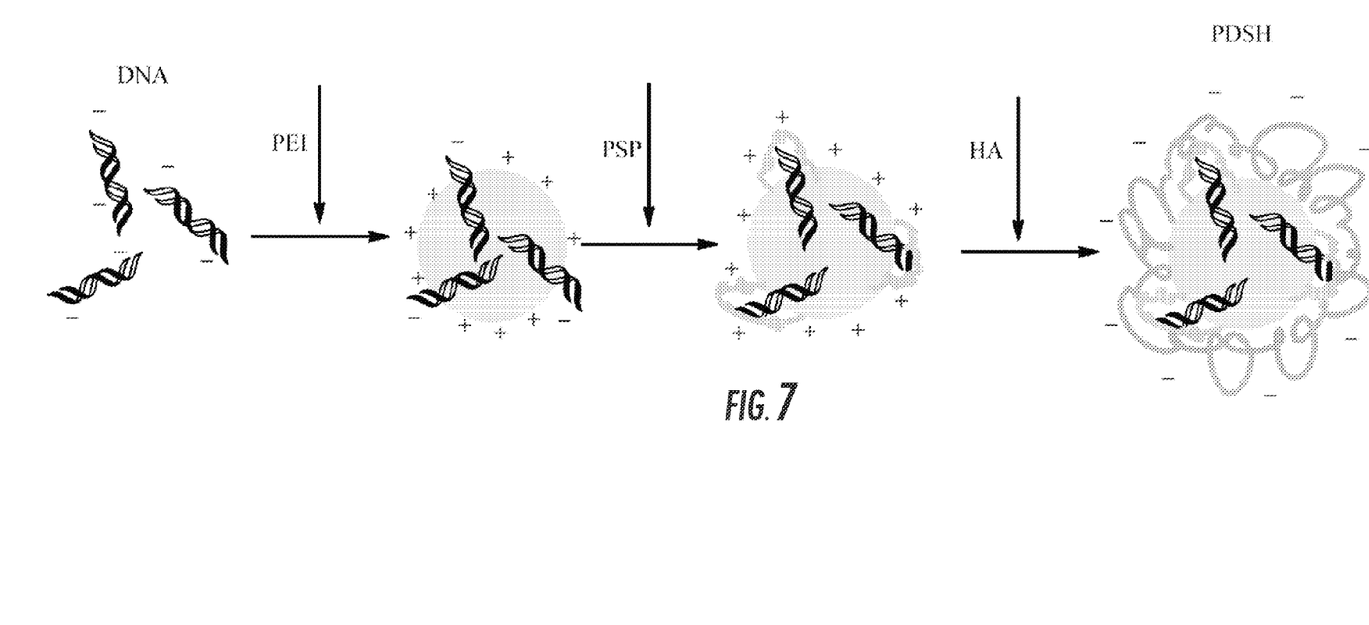
FIG. 7 shows a schematic illustration of one particular embodiment for fabricating clinically effective non-viral gene delivery system (PoSH).

In the particular embodiment shown schematically in FIG. 7, the tetrary gene delivery system is composed of DNA molecules as the delivery molecules, polyethylenimine ("PEI"), polyspermine ("PSP") as the first biocompatible polymer, and hyaluronate ("HA") as the second biocompatible polymer.

The delivery system described herein can be used to transfect a cell with the delivery molecule (e.g., DNA or RNA). Once inside the cell, glutathione (GSH) can release the delivery molecule from the delivery system by exposing the core, uncapping the end of the delivery molecule, and releasing the delivery molecule from the PEI. Glutathione is present at a much higher concentration within the cell as compared to that outside the cell (i.e, a very low concentration of GSH in serum); thus, the delivery molecule can be protected outside of the cell and then released once inside the cell. Glutathione, as is known in the art, is a tripeptide with an unusual peptide linkage between the amine group of cysteine (which is attached by normal peptide linkage to a glycine) and the carboxyl group of the glutamate side-chain, and acts as an antioxidant within the cell. In conjunction with glutathione, the pH inside the cell can also help release the delivery molecule from the system within the cell. Typically, the pH within the cell can be about 7.1 to about 7.7 (e.g., about 7.3 to about 7.5).

Once disassociated from the delivery system, the first and second biocompatible polymers can be released into the cell without harm, since these polymers are compatible with the materials within the cell. Additionally, the PEI polymer is biocompatible with the components of the cell.

Thus, the delivery molecule (e.g., DNA, RNA, or combinations thereof) can be protected within the delivery system outside of the cell, and then released from the delivery system inside of the cell.

EXAMPLES

As discussed below, the particular embodiment shown schematically in FIG. 7 was fabricated such that the tetrary gene delivery system was composed of DNA molecules as the delivery molecules, polyethylenimine ("PEI"), polyspermine ("PSP") as the first biocompatible polymer, and hyaluronate ("HA") as the second biocompatible polymer.

Methods:

Polyspermine (PSP) Synthesis: PSP was synthesized using the Lomant's reagent (LR reagent) as a crosslinker. Spermine (202 mg) was dissolved in 25 mL of dichloromethane in a 100 mL round bottle. LR reagent (404 mg) in 10 mL dichloromethane was slowly added to the spermine solution under stirring. After that, the reaction was kept under reflux at 50° C. for 24 hours. The resulting mixture was purified by dialysis against DI water for 24 hours to yield PSP.

Formation of Ternary Complex: First binary complexes of pDNA with PEI25 (N/P ratio 10) was prepared by incubating the respective solution in 150 mM NaCl at room temperature for 30 min. Then PSP (N/P ratio 10, 20 and 50) and HA (with weight ratios of 1 and 2) were added subsequently to the complexes in 30 min. time interval to get complexes of desired composition. The complexes were suspended in 1 mL, 150 mM NaCl to measure the sizes and zeta potentials with the Nano-ZS Zetasizer (Malvern).

DNA Binding and Cleavage Study: DNA-binding capability of polymers and cleavage of the complexes (prepared as described above) with DTT was evaluated using the agarose gel retardation and dye exclusion assay. For the cleavage study, 20 μL of complexes were incubated with 2 μL of DTT (100 mM) for 3 h. then with 2 μL of heparin (350 units/mL) for 2 h., followed by agarose gel (0.8%) electrophoresis. For dye exclusion study, 10 μL of complexes were mixed with 100 uL of dye (1×SYBR green I) and the fluorescence was measured a microplate reader (DTX 880, Beckman Culter, CA, USA) at $\lambda_{EX}$ 485 and $\lambda_{EM}$ 535 nm.

EGFP Gene Transfection: Transfection efficiency of the polymers was studied in NIH/3T3 cells using EGFP gene as a reporter gene and PEI25 and Lipofectamin2000 as positive control. Cells were seeded at a density of 40,000 cells/well into 24-well plate in 500 μl of DMEM medium (supplemented with 100 U penicillin/streptomycin and 10% FCS) and allowed to reach 70% confluence. Transfection medium was replaced with fresh medium (10, 25 and 50% FCS) just before adding complexes. Then the complexes (prepared as described above) were directly added to the wells (DNA: 1.0 μg/well) and incubated for 24 h. at 37° C. The transfection medium was then replaced with the fresh medium (DMEM: 10% FCS) and the cells were allowed to grow for 48 hour after transfection. Cells were washed (3×) with PBS (pH 7.4), trypsinized (200 μL) for 2 min. and fixed with 500 μL formaldehyde (4% in PBS) for 30 min. The GFP expression was quantified by cytomics FC500 (Beckman Coulter) using FL1 channel ($\lambda_{EX}$=488 and $\lambda_{EM}$=519 nm). Instrument setting was calibrated for each run so as to obtain a background level of EGFP gene expression of 1-2% for control samples (i.e., untreated cells), and the percentage of GFP positive cells was determined relatively. A total of 20,000 gated cells were analyzed.

Cytotoxicity: The cytotoxicity of polymers (PSP and PEI25) and complexes were evaluated with MTT assay. NIH/3T3 cells were seeded in 96-well plates at an initial density of 10,000 cells/well in 200 μl of DMEM medium supplemented with 100 U penicillin/streptomycin and 10% FCS. After 24 hours, the medium was replaced with 200 μl of fresh medium containing polymers (1.0 to 30.0 μg/mL) or the complexes with the composition used for transfection. After 24-hour incubation, MTT reagent and stop solution were added according to the manufacturer's protocol, and the optical density was measured using a microplate reader ($EL_X808$, Bio-Tech Instrument, Inc) at the wavelength of 595 nm to evaluate the cell viability.

Results:

As shown in FIGS. 1-6 and discussed above, the ternary system (PoSH) can achieve high transfection efficiency while with non-toxic effect on the cells with the existence of serum, which makes it a promising tool for gene therapy and creating animal disease model.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of forming a delivery system, comprising:
   binding a DNA or RNA molecule with polyethylenimine such that an end of the DNA or RNA molecule is exposed, wherein the polyethyienimine has a positive electrostatic charge, and wherein the end of the DNA or RNA molecule has a negative electrostatic charge;
   thereafter, capping the end of the DNA or RNA molecule that is exposed with a crosslinked polyspermine, the crosslinked polyspermine having an N/P ratio greater than 5 and wherein the crosslinked polyspermine has been crosslinked via reaction of a polyspermine and a disulfide crosslinker, the crosslinked polyspermine having a positive electrostatic charge such that the crosslinked polyspermine is electrostatically bonded to the end of the DNA or RNA molecule and a core is formed that includes the polyethylenimine, the DNA or RNA molecule, and the crosslinked polyspermine; and encapsulating the core with hyaluronic acid or alginate to form the delivery system, wherein the hyaluronic acid or alginate has a negative electrostatic charge, and wherein the hyaluronic acid or alginate is electrostatically bonded to the core, wherein the hyaluronic acid or alginate is present in a weight ratio of up to 50 comparing the weight of the DNA or RNA molecule.

2. The method of claim 1, wherein the crosslinked polyspermine is crosslinked with dithiobis(succinimidyl propioniate), cystamine bisacrylamide, (bisacryloyloxyethyl) disulfide or derivatives thereof.

3. The method of claim 1, wherein the crosslinked polyspermine has a N/P ratio of 5 to about 50.

4. The method of claim 1, wherein the hyaluronic acid or alginate is present in a weight ratio of 0.2 to about 50 comparing the weight of the DNA or RNA molecule.

5. The method of claim 1, wherein the core is encapsulated with hyaluronic acid.

\* \* \* \* \*